US009916422B2

United States Patent
Haimerl

(10) Patent No.: US 9,916,422 B2
(45) Date of Patent: Mar. 13, 2018

(54) METHOD FOR PLANNING THE POSITIONING OF AN IMPLANT

(75) Inventor: Martin Haimerl, Gilching (DE)

(73) Assignee: Brainlab AG, Munich (DE)

( * ) Notice: Subject to any disclaimer, the term of this patent is extended or adjusted under 35 U.S.C. 154(b) by 474 days.

(21) Appl. No.: 13/979,977

(22) PCT Filed: Jan. 26, 2011

(86) PCT No.: PCT/EP2011/051056
§ 371 (c)(1),
(2), (4) Date: Jul. 16, 2013

(87) PCT Pub. No.: WO2012/100825
PCT Pub. Date: Aug. 2, 2012

(65) Prior Publication Data
US 2013/0304429 A1    Nov. 14, 2013

(51) Int. Cl.
*G06G 7/48* (2006.01)
*G06F 19/00* (2018.01)
*A61B 34/10* (2016.01)
*A61B 90/00* (2016.01)

(52) U.S. Cl.
CPC .......... *G06F 19/3437* (2013.01); *A61B 34/10* (2016.02); *A61B 90/37* (2016.02); *A61B 2034/104* (2016.02)

(58) Field of Classification Search
CPC ..................................................... A61B 34/10
USPC ............................................................ 703/6
See application file for complete search history.

(56) References Cited

U.S. PATENT DOCUMENTS

2009/0316967 A1    12/2009    Dardenne et al.

FOREIGN PATENT DOCUMENTS

WO    2005/000140    1/2005
WO    2006/129087    12/2006

OTHER PUBLICATIONS

Babisch, M.D. et al., "The Rationale for Tilt-Adjusted Acetabular Clip Navigation", The Journal of Bone and Joint Surgery, Inc., 2008, pp. 357-365.
(Continued)

*Primary Examiner* — Hugh Jones
(74) *Attorney, Agent, or Firm* — Tucker Ellis LLP

(57) ABSTRACT

The present invention relates to a method for planning the positioning of an implant relative to a body part, comprising the steps of: —identifying at least one reference feature of the body part and determining, in a first posture of the patient, a biunique positional and/or orientational relationship between the at least one reference feature and at least one adjustment parameter defined for the first posture, for positioning the implant; —identifying the at least one reference feature of the body part in a second posture of the patient; —deriving at least one corresponding adjustment parameter defined for the second posture from the position and/or orientation of the at least one reference feature in the second posture and the positional and/or orientational relationship between the at least one reference feature in the first posture and the at least one adjustment parameter defined for the first posture.

18 Claims, 1 Drawing Sheet

(56) References Cited

OTHER PUBLICATIONS

Zhu et al., "Quantification of Pelvic Tilt in Total Hip Arthroplasty", Clinical Orthopaedics and Related Research, 2010, pp. 571-575.
International Search Report for International Application No. PCT/EP2011/051056 dated Oct. 7, 2011.
M. Tannast, et al. Estimation of Pelvic Tilt on Anteroposterior X-Rays—A Comparison of Six Parameters; Scientific Article; Skeletal Radiol DOI 10.1007/s00256-005-0050-8; Sep. 28, 2005; copyright ISS 2005; 7 Pgs.

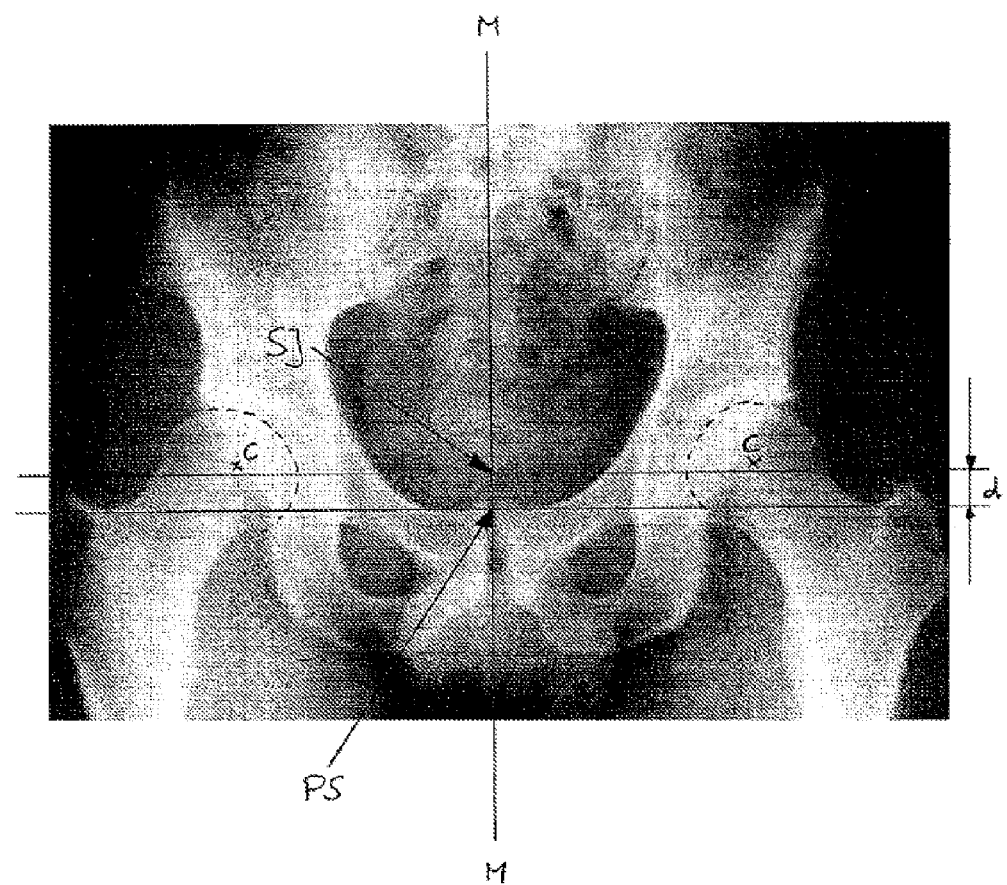

METHOD FOR PLANNING THE POSITIONING OF AN IMPLANT

This application is a national phase of International Application No. PCT/EP2011/051056 filed Jan. 26, 2011 and published in the English language.

The present invention relates to a method for planning the positioning of an implant relative to a body part, wherein one or more adjustment parameters serve as a reference for proper positioning.

Until now, most hip navigation systems have referred to fixed bony co-ordinate systems when inserting the implant: the anterior pelvic plane is for example used as a reference for defining the cup position. However, this plane has been found to significantly deviate from the "true frontal plane" of a patient, see for example Babisch J W, Layher F, Amiot L-P, The Rationale for Tilt-Adjusted Acetabular Cup Navigation, Journal of Bone and Joint Surgery (American) 2008, 90(2):357-365. This deviation is called the pelvic tilt. For surgeries in a supine position, it has been suggested that the relationship between the pelvis and the operating table plane be acquired, so as to estimate and correct for the pelvic tilt in a lying position, see for example Tannast M, Murphy S B, Langlotz F, Anderson S E, Siebenrock K A, Estimation of Pelvic Tilt on Anteroposterior X-rays—a Comparison of Six Parameters, Skeletal Radiology, 2006. Based on this information, the orientation angles (for example, inclination and anteversion) for the cup position can be adjusted and shown to the surgeon.

However, currently used techniques for pelvic tilt correction do not incorporate information which is considered the best reference by most surgeons, namely the pelvic tilt when the patient is in a standing position. This can lead to major inaccuracies. Moreover, the soft tissue laxity during the operation and the position on the operating table may deviate, which can also render these approaches inaccurate. This problem generally occurs when adjustment parameters for positioning an implant are defined for a posture of the patient which differs from the posture of the patient during surgery. Possible postures for a patient include for example a standing posture, a sitting posture and a lying posture.

It is the object of the present invention to provide a method for planning the positioning of an implant by considering adjustment parameters for positioning an implant which are defined in a posture of the patient which differs from the posture of the patient during surgery. More specifically, it is the object of the present invention to provide a method which considers the frontal plane of the patient in a standing posture during artificial hip surgery, in which the patient is in a lying position.

This object is achieved by the subject-matter of independent claims 1, 14 and 15. Dependent claims 2 to 13 define more specific embodiments of the present invention.

The method in accordance with the invention for planning the positioning of an implant relative to a body part comprises the following steps:
  identifying at least one reference feature of the body part and determining, in a first posture of the patient, a biunique positional and/or orientational relationship between the at least one reference feature and at least one adjustment parameter defined for the first posture, for positioning the implant;
  identifying the at least one reference feature of the body part in a second posture of the patient;
  deriving at least one corresponding adjustment parameter defined for the second posture from the position and/or orientation of the at least one reference feature in the second posture and the positional and/or orientational relationship between the at least one reference feature in the first posture and the at least one adjustment parameter defined for the first posture.

In other words, reference features are identified and their relationship to one or more adjustment parameters which help to adjust the implant relative to a body part is determined while the patient is in a first posture, wherein the adjustment parameters are defined for the first posture. According to the present invention, any anatomical landmark can serve as a reference feature. Preferably, landmarks which can easily be identified are chosen as reference features, such as conspicuous bony structures like the anterior superior iliac spines, the upper border of the pubic symphysis, the sacrococcygeal joint or prominences which are formed on the anterior rim of the acetabulum. After the patient and/or the body part has changed its posture to a second posture, corresponding adjustment parameters can be reconstructed for the second posture by identifying the reference features in the second posture, since the relationship between the reference features and the adjustment parameters is known, having been determined in the first posture. Adjustment parameters can for example include a sagittal/median plane, a frontal plane and/or a horizontal plane of the patient or body part.

In another embodiment of the present invention, reference features of the body part are identified in images obtained by means of imaging methods, in particular x-ray imaging methods, and/or by palpating the reference features, in particular by means of a tracked pointer instrument. More specifically, one or more x-ray images can be taken while the patient is standing and reference features can be identified in these x-ray images. These reference features can be subsequently identified, while the patient is in a lying position, by palpating them with a pointer instrument which is tracked by a tracking system known from the prior art. This allows a navigation system to save and store the spatial position and orientation of the palpated reference features for further processing during surgery.

In another embodiment of the present invention, at least one supplementary reference is determined on the basis of the position and/or orientation of at least one reference feature. For example, several points on the socket of an acetabulum can be palpated by a tracked pointer instrument, and this positional information can be transferred to a navigation system which then calculates the centre of rotation of the respective acetabulum. This centre of rotation is then known and can be used in subsequent calculations.

In accordance with another embodiment of the present invention, determining the positional and/or orientational relationship between the at least one reference feature and the at least one adjustment parameter involves determining the positional and/or orientational relationship between at least two reference features and/or supplementary references. In other words, the biunique or one-to-one relationship between the reference features and the adjustment parameters can be determined on the basis of the position and/or orientation of the reference features and/or supplementary references.

In accordance with another embodiment of the present invention, the positional and/or orientational relationship between at least two reference features and/or supplementary features is determined on the basis of direct measurements in 2D images, in particular in a single 2D image. If the image is taken from a known position and/or orientation relative to the patient, it is possible to measure the distance and/or orientation of characteristic features in the image directly and to transfer this information to the navigation system for further processing.

In accordance with another embodiment of the present invention, at least one other adjustment parameter which is defined for the second posture is derived. The adjusted registration specified by the correspondence between the pre-operative and intra-operative data is then used as a reference orientation for further comparisons. If, for example, the pelvic tilt relative to a frontal plane of the patient is known from prior calculations, then the rotation of the pelvis around an anterior-posterior axis can be determined and the respective adjustment parameters can be corrected, wherein only the rotation of the pelvis in a plane parallel to the frontal plane is considered in subsequent calculations.

Moreover, multiple adjustment parameters can be derived in an iterative process, wherein each derivation of an adjustment parameter defined for the second posture takes into account the other adjustment parameter(s) defined for the second posture, so as to optimise the final outcome of registration.

For incomplete or inaccurate measurements, one or more steps for deriving the adjustment parameters can also be performed iteratively in order to optimise the final outcome of registration.

Although the present invention can be performed for any method in which an implant is to be positioned relative to a body part, another embodiment of the present invention is specifically related to artificial hip joint surgery. X-ray images taken in an anterior-posterior direction can be used for pelvic tilt adjustment during navigation. Reference measurements can be taken in the anterior-posterior x-ray images and then combined with navigation information. In particular, cranial-caudal distances between specified landmarks (for example from the pubic symphysis to the upper edge of the sacrococcygeal joint) can be measured in the x-ray image taken of a standing patient before surgery, and this information can be used to adjust for pelvic tilt within the registration/navigation procedure. For this purpose, the corresponding landmarks can be acquired intra-operatively by the navigation system, for example by palpating them with a tracked pointer instrument. The registration can then be adjusted in such a way that the distances measured in the x-ray images are reproduced for the recumbent patient, immediately before or during surgery.

This approach requires that specific measurements be obtained in the anterior-posterior x-ray images so as to guarantee that the degree of freedom which is primarily to be adjusted during registration/navigation can be fixed by means of these measurements, i.e. the measurements have to be in a one-to-one relationship with the parameters which are primarily to be adjusted within the registration/navigation process.

Additionally, other adjustment parameters can be fine-adjusted once a basic correspondence is given between the pre-operative situation in the x-ray image and the intra-operative scenario—rotations around the anterior-posterior axis can for example be corrected if other directional distances can be compared between the pre-operative and intra-operative scenario. The rotation around the anterior-posterior axis can for example be corrected by first measuring the difference in the cranial-caudal direction between reference features such as the upper border of the pubic symphysis and the centre of at least one acetabulum and then reproducing these distances in the intra-operative situation as soon as the orientation of the registration has been corrected for pelvic tilt.

In accordance with the present invention, planes could be defined which are approximately aligned with the projection direction of the x-ray images. For anterior-posterior x-ray images, sagittal or axial planes according to the posture of the pelvis in the x-ray image (taken for example of a patient in an upright standing position) can be used. Preferably, the measurements taken in the image are then vertical (cranial-caudal distances according to the given posture in the x-ray image) for sagittal planes or horizontal (medial-lateral distances according to the given posture on the x-ray image) for axial planes. For proper calculations, the reference features should be reasonably defined in both the pre-operative and intra-operative data, at least in the measurement direction. In order to reduce measurement errors which will affect the desired adjustment parameters, distances measured in the x-ray image should be small (since possible calibration errors can then be reduced) and/or the distances between landmarks/reference features in the projection onto the image plane are high, for example the distance between the pubic symphysis and the sacrococcygeal junction is high in an anterior-posterior direction.

In accordance with a preferred embodiment of the present invention, the cranial-caudal distances between the projections of reference features onto the image plane are used to adjust for pelvic tilt. For example, the cranial-caudal distance from the upper border of the pubic symphysis to the sacrococcygeal junction can be used, or more preferably the distance between the points at which the sacrococcygeal junction and the upper border of the pubic symphysis cross the median plane of the patient on a two-dimensional image. When the patient is in a lying posture, for example intra-operatively, the upper border of the pubic symphysis can be indirectly/virtually constructed from other information. This also applies to reference features other than the upper border of the pubic symphysis. Similar distances could also be used to define tilts or flexion values for other anatomical structures, for example a tilt of the lumbar spine or a flexion in the hip or knee joint.

It is also possible to use angles to define the reference measurements. For two-dimensional images, for example x-ray images, it is helpful if the triangles/planes which are for example spanned by connection lines between reference features and define an angle are somewhat parallel to the projection plane of the image. The angle between the centre plane (and/or the centre line projected onto the anterior-posterior plane) and the connection line between one anterior superior iliac spine point and the centre point of the upper border of the pubic symphysis could for example be used, since this angle is defined in the anterior pelvic plane, which is considered to be reasonably close to the frontal plane according to the posture of the pelvis in an anterior-posterior x-ray image. In this case, the angle which should be used is not the three-dimensional angle but rather the angle between lines projected onto the image plane, since only this angle can be measured in the two-dimensional x-ray image. The registration procedure must then first be adjusted to reflect the posture given in the x-ray image, before the intra-operative calculation can be performed accordingly.

Distance measurements can also be used to derive more than one adjustment parameter iteratively. The cranial-caudal distance (according to the given posture in the x-ray image) between the upper border of the pubic symphysis and the centre of rotation of the hip joint or an alternative reference point can for example be used to adjust for a rotation within the frontal plane according to the posture given in the x-ray image. Points at the acetabulum which are clearly defined in terms of their cranial-caudal position, for example the inferior prominence of the acetabular rim, can be used as alternative reference features.

FIG. 1 shows a two-dimensional x-ray image which has been taken in an anterior-posterior direction and depicts a pelvis of a patient standing in an upright position.

Since the image was taken in an anterior-posterior direction, the true frontal plane of the patient is parallel to the image plane.

Several reference features can be identified in the image which for example help to derive at least one corresponding adjustment parameter defined for a lying position of the patient. These could for example be the sacrococcygeal junction and the upper border of the pubic symphysis. The median plane M of the patient is indicated in the image, wherein the points at which the sacrococcygeal junction and the upper border of the pubic symphysis cross the median plane M in the two-dimensional image are denoted as SJ and PS, respectively. The distance d between the points SJ and PS in a cranial-caudal direction, i.e. along the median plane in the 2D image, is measured and used to determine a biunique positional and/or orientational relationship between the reference features and the frontal plane of the patient. Moreover, the shape of the left and right acetabulum can be identified in the x-ray image, such that a centre of rotation C can be calculated for both the left and right acetabulum.

The invention claimed is:

1. A method for planning the positioning of an implant relative to a body part of an associated patient, comprising:
   acquiring, by a navigation system, pre-operative two-dimensional (2D) imaging data of the body part of the associated patient, the associated patient having been positioned in a first posture;
   identifying, via the navigation system and based on the pre-operative 2D imaging data, at least one reference feature of the body part of the associated patient;
   determining, by the navigation system, first posture relationship data comprising a one-to-one relationship between the at least one reference feature of the body part of the associated patient and at least one adjustment parameter defined for the first posture, for positioning the implant;
   acquiring, by the navigation system, intra-operative tracking position data comprising a position, in three-dimensional (3D) space, of the at least one reference feature of the body part of the associated patient while the associated patient is positioned in a second posture, the second posture differing from the first posture, the intra-operative tracking position data including palpating the at least one reference feature with a tracked pointer instrument;
   generating, by the navigation system, at least one corresponding adjustment parameter for the second posture based on the intra-operative tracking position data and the first posture relation data; and
   planning, via the navigation system, the positioning of the implant relative to the body part of the associated patient based on the at least one corresponding adjustment parameter for the second posture.

2. The method according to claim 1, further comprising:
   identifying, via the navigation system, at least one supplementary reference feature based on the pre-operative 2D imaging data and a position of the at least one reference feature.

3. The method according to claim 2, further comprising:
   determining, by the navigation system, a relative position between the at least one reference feature and the at least one adjustment parameter by determining the relative position between at least two reference features and/or supplementary reference features.

4. The method according to claim 3, wherein the relative position between the at least two reference features and/or supplementary reference features is determined on the basis of direct measurements, by the navigation system, in the pre-operative 2D imaging data.

5. The method according to claim 4, wherein the relative position between the at least two reference features and/or supplementary features is determined on the basis of the direct measurements in a single 2D image.

6. The method according to claim 1, wherein the first posture is a standing posture and the second posture is a lying posture.

7. The method according to claim 1, wherein at least one other adjustment parameter that is defined for the second posture is derived.

8. The method according to claim 7, wherein at least one adjustment parameter defined for the second posture is taken into account in order to derive at least one other adjustment parameter defined for the second posture.

9. The method according to claim 8, wherein the adjustment parameters are derived in an iterative process, wherein each derivation of an adjustment parameter defined for the second posture takes into account the other adjustment parameter(s) defined for the second posture.

10. The method according to claim 1, wherein the body part is a human pelvis and the implant is a cup of an artificial hip joint.

11. The method according to claim 10, wherein the pre-operative 2D imaging data is an x-ray image, the x-ray image being acquired in an anterior-posterior direction prior to surgery.

12. The method according to claim 11, wherein the x-ray image is a single x-ray image.

13. The method according to claim 10, wherein a frontal plane, a sagittal plane and/or a horizontal plane is/are defined as the adjustment parameter(s) defined for the first posture.

14. The method according to claim 10, wherein the sacrococcygeal junction, the upper border of the pubic symphysis the center of at least one acetabulum and/or at least one anterior superior iliac spine serve(s) as the reference feature(s).

15. The method according to claim 14, wherein the upper border of the pubic symphysis is the points at which the sacrococcygeal junction and the upper border of the pubic symphysis cross the median plane of the patient in the 2D image.

16. The method according to claim 1, wherein the pre-operative 2D imaging data is an x-ray image, and wherein at least one plane is defined that is approximately aligned with a projection direction of the x-ray image.

17. A method for planning positioning of an implant relative to a body part of an associated patient comprising:
   acquiring, by a navigation system, pre-operative two-dimensional (2D) imaging data of the body part of the associated patient, the associated patient having been positioned in a standing posture;
   identifying, via the navigation system and based on the pre-operative 2D imaging data, at least one reference feature of the body part of the associated patient;

determining, by the navigation system, standing posture relationship data comprising a one-to-one relationship between the at least one reference feature of the body part of the associated patient and at least one adjustment parameter defined for the standing posture, for positioning the implant;

acquiring, by the navigation system, intra-operative tracking position data comprising a position, in three-dimensional (3D) space, of the at least one reference feature of the body part of the associated patient while the associated patient is positioned in a lying posture, the intra-operative tracking position data including palpating the at least one reference feature with a tracked pointer instrument;

generating, by the navigation system, at least one corresponding adjustment parameter for the lying posture based on the intra-operative tracking position data and the standing posture relationship data; and planning, via the navigation system, the positioning of the implant relative to the body part of the associated patient based on the at least one corresponding adjustment parameter for the lying posture.

18. A system comprising:

a navigation system;

a pointer instrument configured to be tracked by the navigation system, wherein the navigation system is configured to:
acquire pre-operative two-dimensional (2D) imaging data of a body part of an associated patient, the associated patient having been positioned in a first posture;
identify, based on the pre-operative 2D imaging data, at least one reference feature of the body part of the associated patient;
determine first posture relationship data comprising a one-to-one relationship between the at least one reference feature of the body part of the associated patient and at least one adjustment parameter defined for the first posture, for positioning the implant;
acquire intra-operative tracking position data comprising a position, in three-dimensional (3D) space, of the at least one reference feature of the body part of the associated patient while the associated patient is positioned in a second posture, the second posture differing from the first posture, the intra-operative tracking position data including palpating the at least one reference feature with the pointer instrument;
generate at least one corresponding adjustment parameter for the second posture based on the intra-operative tracking position data and the first posture relationship data; and
plan the positioning of the implant relative to the body part of the associated patient based on the at least one corresponding adjustment parameter for the second posture.

* * * * *